United States Patent [19]

Marchionni et al.

[11] Patent Number: 5,371,272
[45] Date of Patent: Dec. 6, 1994

[54] PROCESS FOR PREPARING FUNCTIONALIZED PERFLUOROPOLYOXYALKYLENES

[75] Inventors: Giuseppe Marchionni, Milan; Ugo De Patto, Cogliate, both of Italy

[73] Assignee: Ausimont S.p.A., Milan, Italy

[21] Appl. No.: 68,960

[22] Filed: May 28, 1993

[30] Foreign Application Priority Data

May 29, 1992 [IT] Italy ............. MI92 A 001318

[51] Int. Cl.$^5$ ............................................. C07C 69/708
[52] U.S. Cl. ..................................... 560/180; 560/192; 560/227
[58] Field of Search .................... 560/180, 192, 227

[56] References Cited

U.S. PATENT DOCUMENTS

| | | | |
|---|---|---|---|
| 3,810,874 | 5/1974 | Mitsch et al. | 260/75 H |
| 3,847,978 | 11/1974 | Sianesi et al. | 260/535 H |
| 4,085,137 | 4/1978 | Mitsch et al. | 260/561 HL |
| 4,668,357 | 5/1987 | Marchionni et al. | 204/157.92 |
| 4,721,795 | 1/1988 | Caporiccio et al. | 549/445 |
| 4,757,145 | 7/1988 | Caporiccio et al. | 546/81 |

FOREIGN PATENT DOCUMENTS

| | | |
|---|---|---|
| 0340739 | 11/1989 | European Pat. Off. . |
| 1104482 | 2/1968 | United Kingdom . |
| 1226566 | 3/1971 | United Kingdom . |

*Primary Examiner*—José G. Dees
*Assistant Examiner*—Barbara S. Frazier
*Attorney, Agent, or Firm*—Bryan Cave

[57] ABSTRACT

A process for preparing functionalized perfluoropolyoxyalkylenes, wherein the corresponding perfluoropolyoxyalkylenes containing peroxy bonds in the chain are reacted with a primary or a secondary alcohol, or mixtures of these alcohols, in the presence of a catalyst selected from iodine, hydriodic acid or alkali metal iodides. The process leads to the obtainment of perfluoropolyoxyalkylenes having a high functionalization degree, which can be easily purified by removing the excess of alcohol through distillation.

7 Claims, No Drawings

PROCESS FOR PREPARING FUNCTIONALIZED PERFLUOROPOLYOXYALKYLENES

The present invention relates to a process for preparing functionalized perfluoropolyoxyalkylenes via reduction of perfluoropolyoxyalkylenes containing peroxy bonds in the chain.

High molecular weight perfluoropolyoxyalkylenes having peroxy bonds —O—O— along the chain are products well known in the art. Said products can be converted, through reduction of the peroxy bonds, into regulated molecular weight perfluoropolyoxyalkylene compounds having end groups functionalized with carboxylic groups and/or ketonic groups, or functional groups derived therefrom, such as acyl halides, esters, amides, nitriles, carboxylated groups, hemiketals, etc.

Functionalized perfluoropolyoxyalkylenes are described, for example, in U.S. Pat. Nos. 4,085,137; 4,721,795 and 4,757,145. They are used in several fields either as such (for example as lubricants or as protective agents for lapideous materials or for metals), or as starting compounds for the synthesis of other fluorinated products, and in particular of condensation polymers, endowed with unusual chemico-physical characteristics, such as thermal stability, chemical inertia, high flexibility even at very low temperatures, etc.

In view of such utilizations it is of substantial importance to provide a process for the reduction of the peroxide bridges, which can be easily practised on an industrial scale and which leads to the obtainment of products having the highest possible purity degree as well as a high functionalization degree.

U.S. Pat. No. 3,847,978 describes a broad class of products which can act as reducing agents for the peroxide bridges, among which: molecular hydrogen, nascent hydrogen; primary or secondary alcohols, either alone or in the presence of aluminium alcoholates; metal hydrides or complexes thereof; sulphur dioxide; hydrosulphurous acid or sulphides; metals, such as iron or tin, in the presence of a strong acid; hydriodic acid, and still other products.

In the industrial practice, not all of these reducing agents permit to obtain satisfactory results, both due to the too low reaction rate and due to the formation of by-products, which reduce the purity degree and the functionalized product yields.

One of the utilized processes comprises the use of $SO_2$ as a reducing agent, in the presence of catalytic amounts of $I_2$ or HI. Such process, although it provides perfluoropoly-oxyalkylenes endowed with a high functionalization degree, gives rise to $SO_3$, a chemically aggressive substance, which must be removed from the final product by means of repeated washings, what lowers the final yield and rises problems connected with the disposal of the wastes. Analogous problems related to the purification of the final product are encountered if HI is used as a reducing agent, because that leads to the formation of $I_2$ which too can be removed only by means of repeated washings.

A further disadvantage of the above-mentioned processes derives from the use of chlorofluorocarbons, for example CFC 113 ($CCl_2F-CClF_2$), as a reaction medium, what involves environmental problems, particularly as regards the ozone layer of the atmosphere.

As already mentioned, U.S. Pat. No. 3,847,978 suggests to use, as reducing agents, primary or secondary alcohols, such as methanol, ethanol, isopropanol. Apart from the fact that with the alcohols suggested by the above-said patent the reaction rate is very low (for example, if methanol is used, the reaction is completed only after 30 hours at reflux), the reaction with alcohols gives rise to high amounts of hydrogenated end groups of the type —$CF_3H$, with consequent lowering of the functionalization degree of the final products and loss of a carbon atom.

It has now surprisingly been found that the reaction for reducing perfluoropolyoxyalkylene containing peroxy bonds in the chain can be advantageously conducted with primary or secondary alcohols, in the presence of a catalyst selected from iodine, hydriodic acid or alkali metal iodides, with formation of high-functionalization-degree perfluoropolyoxyalkylenes, which can be easily purified by removing the alcohol in excess through distillation.

Thus, it is an object of the present invention to provide a process for preparing functionalized perfluoropolyoxyalkylenes, which comprises reacting the corresponding perfluoropolyoxyalkylenes containing peroxy bonds in the chain with a primary or secondary alcohol R—OH, or mixtures of these alcohols, in the presence of a catalyst selected from iodine, hydriodic acid or iodides of alkali metals.

The peroxy perfluoropolyoxyalkylenes utilized as starting products are preparable in accordance with what is described, for example, in GB patent Nos. 1,226,566 and 1,104,482, and correspond to the general formula:

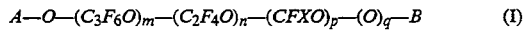

$$A—O—(C_3F_6O)_m—(C_2F_4O)_n—(CFXO)_p—(O)_q—B \qquad (I)$$

where: A and B, like or different from each other, are end groups selected from: —COF, —$CF_2$—COF, —CF($CF_3$) —COF, —$CF_2$—CO—$CF_3$, —$CF_2CF_2$—COF, —$CF_3$, —$C_3F_7$, —$CF_2Cl$, —$C_2F_4Cl$, —$C_3F_6Cl$;

X is selected from: —F, —$CF_3$;

m, n, p are integers, like or different from one another, ranging from 0 to 100, provided that m+n>0; q ranges from 1 to 90, provided that (m+n+p) >q; the various repeating units —$C_3F_6O$—, —$C_2F_4O$, —CFXO— and —O— being statistically distributed along the chain.

In particular, depending On the type of monomers which are present in the chain, the variables m, n, p and q can assume the following values:

(1) when n=0: —X=—F; —$CF_3$; m/p>3; (m+p)/q=2-100;

(2) when m=0: —X=—F; n/p=0.02-50; (n+p)/q=2-1,000;

(3) when m, n, p are other than zero: m/p=0.02-50; m/(n+p)=0.02-50; )m+n+p)/q=2-1,000.

The perfluoropolyoxyalkylene containing peroxide bridges can be utilized as such if the peroxide oxygen content is already at the desired values as a function of the nolecular weight of the functionalized perfluoropolyoxyalkylene compound to be obtained. If the precursor has a peroxide oxygen content which exceeds the one desired, it can be reduced by subjecting the product to a thermal or photochemical treatment according to what is described for example, in U.S. Pat. No. 4,668,357 patent application As reducing agents it is possible to utilize all the primary or secondary alcohols R—OH, in which R is a straight or branched alkyl or cycloalkyl radical having 1 to 12 carbon atoms. Among them, there are utilizable, for example: methanol, ethanol, 1-propanol, 2-propanol, 1-butanol, 2-butanol, 1-hexanol, 2-hexanol, cyclohexanol, 1-dodecanol, 2-dodecanol, etc., or mixtures thereof. The alcohol is used in such amounts that the molar ratio between alcohol and peroxide oxygen (q) generally ranges from 4 to 200, preferably from 10 to 150.

In a preferred embodiment there are used, as reducing agents, the primary alcohols having 4 to 6 carbon atoms or the secondary cycloalkyl alcohols having 5 to 8 carbon atoms. The use of such alcohols permits to sensibly increase the reaction rate so as to obtain a complete conversion in 3–5 hours at the reflux temperature of the alcohol. Particularly preferred are 1-butanol and cyclohexanol.

The reaction is conducted in the presence of catalytic amounts of iodine, hydriodic acid or alkali metal iodides. By "catalytic amounts" are generally meant such catalyst amounts wherefore the ratio between moles of iodine and moles of peroxide oxygen (q) ranges from 0.01 to 0.5, preferably from 0.01 to 0.35. Examples of alkali metal iodides utilizable as catalysts are potassium iodide and sodium iodide.

It is to be noted that the catalyst has not the function of increasing the total reduction reaction rate, but of directing the reaction towards the obtainment functionalized end groups, fully avoiding the formation of hydrogenated end groups —CF$_2$H. In this way it is possible to completely convert the starting peroxide product into a mixture of perfluoropolyoxyalkylenes functionalized at the ends with ester groups:

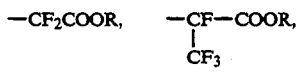

or ketonic groups:

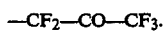

Such end groups can be easily converted, through well known reactions of the art (see for example U.S. Pat. No. 3,810,874), into other reactive functions, such as carboxylic, acylic, amidic, nitrilic, carboxylated, hemiketalic, alcoholic groups, etc.

The process of the present invention is advantageously conducted by using the alcohol itself as a reaction medium: in this way it is possible to avoid using other solvents, such as the chlorofluorocarbons, with considerable advantages as regards both the simplicity and profitability of the process and possible problems connected with the environmental pollution. However, that does not exclude the possibility of practising the process using, as a reaction medium, other solvents, such as carboxylic acids, perfluoropolyethereal alcohols, perfluoropolyethereal esters, etc. The reaction is generally conducted at the reaction medium reflux temperature, so that it is depending on the type of the utilized alcohol and/or solvent; generally, the reaction temperature ranges from 50° to 150° C., while the pressure is generally in the range of from 1 to 10 atm.

At the end of the reaction, the final product can be easily isolated and purified through distillation, preferably at reduced pressure, of the unreacted alcohol.

The following examples are given to better illustrate the present invention, but they are not to be construed as limitative of the scope thereof.

EXAMPLE 1

260 g of 1-butanol, 1 g of iodine and 200 g of a peroxy perfluoropolyoxyalkylene corresponding to general formula (I), wherein m =O, —X : —F, (n+p)/q=13.06 and n/p =1.14, having an average molecular weight equal to 82,000, were charged, at room temperature, into a 1 1 reactor. Through $^{19}$F NMR analysis, the following composition for end groups A and B was determined: —COF (28%), —CF$_2$COF (17%), —CF$_3$ (32%), —CF$_2$Cl (12%), —C$_2$F$_4$Cl (11%).

The reaction mixture was subjected to stirring was heated to reflux temperature in a thermostatic bath over the course of 5 hours. On conclusion of the reaction, the alcohol in excess was removed by distillation up to 100° C. at a reduced pressure of 10 millibars. Them were obtained 199.7 g (yield 99.8%) of perfluoropolyoxyalkylene product, which, on $^{19}$F NMR analysis, resulted to be free from peroxy groups and exhibited an average molecular weight equal to 1,260 and a n/p ratio equal to 1.05. The end groups had the following distribution: —CF$_2$COO(CH$_2$)$_3$CH$_3$ (98.5%), —CF$_3$ (0.9%), —CF$_2$Cl (0.3%), —C$_2$F$_4$Cl (0.3%). —CF$_2$H end groups were absent.

EXAMPLE 2 (comparative)

200 g of the peroxy perfluoropolyoxyalkylene of example 1 and 260 g of 1-butanol were charged into a 1 liter reactor at room temperature.

The reaction mixture was stirred and heated to reflux temperature in a thermostatic bath during 5 hours. At the end of the reaction, the alcohol in excess was removed by distillation at reduced pressure. There were obtained 193 g of product (yield: 96.5%), which, on $^{19}$F NMR analysis, resulted to be free from peroxy groups and exhibited an average molecular weight equal to 1,200 and a n/p ratio equal to 1.04. The end groups were distributed as follows: —CF$_2$COO(CH$_2$)$_3$CH$_3$ (72.4%), —CF$_2$H (26.3%), —CF$_3$ (0.8%), —CF$_2$Cl (0.3%), —C$_2$F$_4$Cl (0.2%).

EXAMPLE 3

200 g of the peroxy perfluoropolyoxyalkylene utilized in example 1, 260 g of 2-butanol and 1 g of I$_2$ were charged into a 1 liter reactor. The mixture was stirred and heated for 15 hours to reflux temperature in a thermostatic bath. At the end of the reaction, the unreacted alcohol was removed by distillation at reduced pressure. Obtained were 197.5 9 (yield: 98.7%) of perfluoropolyoxyalkylene product, which, on $^{19}$F NMR analysis, resulted to be a 2-butanol diester, free from peroxy bridges and from —CF$_2$H end groups. The average molecular weight was equal to 1,230.

EXAMPLE 4

Following the same procedure of example 3, there were reacted 20 g of the peroxy perfluoropolyoxyalkylene utilized in example 1, 65 g of 1-dodecanol and 0.1 g of I$_2$. By heating under stirring in a thermostatic bath at 130° C. for 10 hours, 84.3 g of product were obtained. After removal, under vacuum, of the unreacted alcohol, 19.8 g (yield=99%) of perfluoropolyoxyalkylene product were obtained, which, subjected to $^{19}$F NMR analysis, resulted to be a 1-dodecanol diester, free from peroxy bridges and from —CF$_2$H end groups. The average molecular weight was equal to 1,350.

EXAMPLE 5

200 g of the peroxy perfluoropolyoxyalkylene utilized in example 1,350 g of cyclohexanol and 1 g of I$_2$ were charged into a 1 liter reactor. The mixture was stirred and it was heated for 3 hours at a temperature of 120° C. in a thermostatic bath. On conclusion of the reaction, the unreacted alcohol was removed by distillation at reduced pressure. There were obtained 199.5 g (yield: 99.7%) of perfluoropolyoxyalkylene product which, on $^{19}F$ NMR analysis, resulted to be a cyclohexanol diester free from peroxide bridges and of $-CF_2H$ end groups. The average molecular weight was equal to 1,230.

EXAMPLE 6

260 g of 1-butanol, 1 g of iodine and 200 g of a perfluoropolyoxyalkylene corresponding to general formula (I), where $n=0$, $(m+p)/q=49.3$ and $m/p=23.3$, having an average molecular weight equal to 565, were introduced into a 1 liter reactor. By means of lgF NMR analysis, the following composition for end groups A and B was determined: $-COF$ (9.5%), $-CF_2COF$ (45%), $-CF_3$ (3.5%), $-C_3F_6Cl$ (42%).

The reaction mixture was subjected to stirring and heated to reflux temperature in a thermostatic bath for 5 hours. At the end of the reaction, after removal of the alcohol in excess by distillation at reduced pressure, there were obtained 197.9 g (yield=98.9%) of Perfluoropolyoxyalkylene product, which, on $^{19}F$ NMR analysis, resulted to be free from peroxy groups and exhibited an average molecular weight equal to 535 and a m/p ratio =23. The end groups had the following distribution: $-CF_2COO(CH_2)_3CH_3$ (51.5%), $-CF(CF_3)COO(CH_2)_3CH_3$ (2.5%), $-CF_2COCF_3$ (3%), $-CF_3$ (3.3%), $-C_3F_6Cl$ (39.7%). $-CF_2H$ end groups were absent.

EXAMPLE 7

260 g of 1-butanol, 1 g of iodine and 200 g of a perfluoropolyoxyalkylene corresponding to general formula (I), where m, n, p are other than zero, $(m+n+p)/q=13.0$, $n/p=4.8$, $m/(n+p)=1.03$, and having an average molecular weight equal to 2,950, were charged into a 1 liter reactor at room temperature. Through $^{19}F$ NMR analysis, the following composition was determined for end groups A and B: $-COF$ (47%), $-CF_3$ (53%).

The reaction mixture was subjected to stirring and was heated to reflux temperature in a thermostatic bath during 5 hours. At the end of the reaction, after the alcohol in excess had been removed by distillation at reduced pressure, there were obtained 199.3 g (yield=99.6%), which, on $^{19}F$ NMR analysis, resulted to be free from peroxy groups and exhibited an average molecular weight equal to 1,200 and n/p ratios =2.8 and $m/n+p=1.5$. The end groups had the following composition: $-CF_2COO(CH_2)_3CH_3$ (50%), $-CF(CF_3)COO(CH_2)_3CH_3$ (15%), $-CF_2COCF_3$ (8.5%), $-CF_3$ (26.5%). No end groups $-CF_2H$ were present.

We claim:

1. A process for preparing perfluoropolyoxyalkylenes having ester or ketonic end groups, which comprises reacting the corresponding perfluoropolyoxyalkylenes containing, in the chain, peroxy bonds, with a primary or secondary alcohol R—OH, or mixtures thereof, where R is a straight or branched alkyl or cycloalkyl radical having 1 to 12 carbon atoms, in the presence of a catalytic amount of a catalyst selected from the group consisting of iodine, hydroiodic acid or alkali metal iodides, said catalytic amount being such that the ratio of the number of moles of iodine atoms to the number of moles of peroxide oxygen from ranges from 0.01–0.5.

2. The process of claim 1, wherein the perfluoropolyoxyalkylenes containing peroxy bonds in the chain have the general formula:

$$A-O-(C_3F_6O)_m-(C_2F_4O)_n-(CFXO)_p-(O)_q-B \quad (I)$$

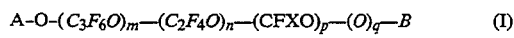

A and B, like or different from each other, are end groups selected from: $-COF$, $-CF_2-COF$, $-CF(CF_3)-COF$, $-CF_2-CO-CF_3$, $-CF_2CF_2-COF$, $-CF_3$, $-C_2F_5$, $-C_2F_5$, $-C_2Cl$, $-C_2F_4Cl$, $-C_3F_6Cl$; X is selected from: $-F$, $-CF_3$, m, n, p are integers, like of different from one another, ranging between 0 and 100, on conditions that $m+n>0$;

q is ranging between 1 and 90, on conditions that $(m+n+p)>q$; the various repeating units $-C_3F_6O-$, $-C_2F_4O$, $-CFXO$ and $-O-$ being statistically distributed along the chain.

3. The process of claim 1, wherein ROH is a primary alcohol having 4 to 6 carbon atoms, or a secondary cycloalkyl alcohol having 5 to 8 carbon atoms.

4. The process of claim 1, wherein the molar ratio of alcohol to peroxide oxygen (q) ranges from 4 to 200.

5. The process of claim 4, wherein the molar ratio of alcohol to peroxide oxygen (q) ranges from 10 to 150.

6. The process of claim 1 wherein the ratio of the number of moles of iodine atoms to the number of moles of peroxide oxygen atoms from 0.01 to 0.35.

7. The process of claim 1, wherein the alcohol is the reaction medium and it is removed by distillation at the end of the reaction.

* * * * *

UNITED STATES PATENT AND TRADEMARK OFFICE
CERTIFICATE OF CORRECTION

PATENT NO. : 5,371,272
DATED : December 6, 1994
INVENTOR(S) : Marchioni, et al

It is certified that error appears in the above-indentified patent and that said Letters Patent is hereby corrected as shown below:

| Column | Line | Delete | Insert |
|---|---|---|---|
| 6 | 18 | "from" | --atoms-- |
| 6 | 47 |  | --ranges-- after atoms |

| Column | Line | Delete | Insert |
|---|---|---|---|
| 6 | 25 |  | -- where: -- |
| 6 | 29 | "$-C_2F_5$" | -- $-C_3F_7$ -- |
| 6 | 29 | "$-C_2Cl$" | -- $-CF_2Cl$ -- |

Signed and Sealed this

Fourth Day of April, 1995

Attest:

BRUCE LEHMAN

*Attesting Officer*   *Commissioner of Patents and Trademarks*